US009681661B2

(12) United States Patent
Pfenning et al.

(10) Patent No.: US 9,681,661 B2
(45) Date of Patent: Jun. 20, 2017

(54) METHOD OF CONTROLLING PARASITIC WEEDS WITH MIXTURES COMPRISING HERBICIDAL ACETOLACTATE SYNTHASE INHIBITORS AND PLANT GROWTH REGULATORS

(75) Inventors: Matthias Pfenning, Schwegenheim (DE); Hagen Bremer, Speyer (DE)

(73) Assignee: BASF Agrochemical Products B.V., Arnhem (NL)

( * ) Notice: Subject to any disclaimer, the term of this patent is extended or adjusted under 35 U.S.C. 154(b) by 0 days.

(21) Appl. No.: 14/343,913

(22) PCT Filed: Sep. 10, 2012

(86) PCT No.: PCT/EP2012/067652
§ 371 (c)(1),
(2), (4) Date: Mar. 10, 2014

(87) PCT Pub. No.: WO2013/037735
PCT Pub. Date: Mar. 21, 2013

(65) Prior Publication Data
US 2014/0228216 A1    Aug. 14, 2014

(30) Foreign Application Priority Data

Sep. 13, 2011 (EP) .................................... 11181041

(51) Int. Cl.
| A01N 43/50 | (2006.01) |
| A01N 37/10 | (2006.01) |
| A01N 43/56 | (2006.01) |
| A01N 37/42 | (2006.01) |
| A01N 47/36 | (2006.01) |
| A01N 47/24 | (2006.01) |

(52) U.S. Cl.
CPC .............. *A01N 43/50* (2013.01); *A01N 37/10* (2013.01); *A01N 37/42* (2013.01); *A01N 43/56* (2013.01); *A01N 47/36* (2013.01)

(58) Field of Classification Search
None
See application file for complete search history.

(56) References Cited

U.S. PATENT DOCUMENTS

| 7,521,395 | B2 * | 4/2009 | O'Neal et al. ............... 504/134 |
| 2005/0044587 | A1 | 2/2005 | Gabard et al. |
| 2008/0269058 | A1 | 10/2008 | Cotterill |
| 2009/0105073 | A1 * | 4/2009 | Taranta et al. ............... 504/100 |
| 2010/0210467 | A1 | 8/2010 | Kobayashi et al. |
| 2010/0304971 | A1 | 12/2010 | Hacker et al. |
| 2011/0028324 | A1 | 2/2011 | Cordingley et al. |

FOREIGN PATENT DOCUMENTS

| CA | 1283553 | 4/1991 |
| DE | 19834627 | 12/1998 |
| EP | 0123001 | 10/1984 |
| EP | 0224441 | 6/1987 |
| EP | 1088480 | 4/2001 |
| WO | WO 03012115 | 2/2003 |
| WO | WO 2008124431 | 10/2008 |

OTHER PUBLICATIONS

Beam et al., "Interaction of Prohexadione Calcium with Agrichemicals Applied to Peanut (*Arachis hypogaea* L.)," Peanut Science, vol. 29, No. 1, (2002), pp. 29-35, Search Report.
Fan et al., "Prohexadione-Calcium Induces Sunflower (*Helianthus annuus*) Resistance Against the Root Parasitic Weed *Orobanche cumana*," Weed Research, vol. 47, No. 1, (2007), pp. 34-43, Search Report.
International Preliminary Report on Patentability, issued in PCT/EP2012/067652, dated Mar. 27, 2014.
International Search Report, issued in PCT/EP2012/067652, dated Jan. 14, 2013.
Krawczyk, "Studies on Effectivity on Application of Tank-Mixture Florasulam with Growth Regulators in the Weed Control in Winter Wheat," Progress in Plant Protection, vol. 46, No. 2, (2006), pp. 200-204, Search Report; Abstract.
Miziniak et al., "Effect of Sulfosulfuron + Retardants Mixtures on Growth and Yield of Winter Wheat and Apera Spica-Venti Control," Progress in Plant Protection, vol. 48, No. 2, (2008), pp. 635-639, Search Report; Abstract.

* cited by examiner

*Primary Examiner* — Richard Schnizer
*Assistant Examiner* — Katherine Peebles
(74) *Attorney, Agent, or Firm* — Brinks Gilson & Lione

(57) ABSTRACT

The present invention relates to a method for controlling parasitic weeds, comprising applying to the host plant, the weeds and/or their habitat herbicidal mixtures or compositions comprising one, two or three acetolactate synthase (ALS) inhibitor(s) and one, two or three plant growth regulator(s) (PGR) which act as ethylene modulators. The present invention also relates to a method for improving the yield of the crop plant comprising applying to the host plant, and/or their habitat mixtures comprising components as defined herein. The present invention also relates to herbicidal mixtures comprising one, two or three acetolactate synthase (ALS) inhibitor(s) selected from imazamox or tribenuron-methyl and one, two or three plant growth regulator(s) (PGR) selected from prohexadione, prohexadione-calcium, trinexapac or trinexapac-ethyl, compositions comprising said mixtures and their use for the control of parasitic weeds.

13 Claims, No Drawings

METHOD OF CONTROLLING PARASITIC WEEDS WITH MIXTURES COMPRISING HERBICIDAL ACETOLACTATE SYNTHASE INHIBITORS AND PLANT GROWTH REGULATORS

This application is a National Stage application of International Application No. PCT/EP2012/067652, filed Sep. 10, 2012, the entire contents of which is hereby incorporated herein by reference. This application also claims priority under 35 U.S.C. §119 to European Patent Application No. 11181041.2, filed Sep. 13, 2011, the entire contents of which is hereby incorporated herein by reference.

The present invention relates to a method for controlling parasitic weeds, comprising applying to the host plant, the weeds and/or their habitat herbicidal mixtures or compositions comprising one, two or three acetolactate synthase (ALS) inhibitor(s) and one, two or three plant growth regulator(s) (PGR) which act as ethylene modulators. The present invention also relates to a method for improving the yield of the crop plant comprising applying to the host plant, and/or their habitat mixtures comprising components as defined herein. The present invention also relates to herbicidal mixtures comprising one, two or three acetolactate synthase (ALS) inhibitor(s) selected from imazamox or tribenuron-methyl and one, two or three plant growth regulator(s) (PGR) selected from prohexadione, prohexadione-calcium, trinexapac or trinexapac-ethyl, compositions comprising said mixtures and their use for the control of parasitic weeds.

Parasitic weeds derive some or all of their sustenance from another plant by penetrating the host's tissue and drawing nutrients from the host plant (W. Koch, M. Kunisch, PLITS 1989/7 (2), *Principles of Weed Management*, 22-26). This occurs either through the stem, e.g. in *Cuscuta* spp., or from the root tissue, e.g. *Striga* spp. (witchweeds) and *Orobanche* spp. (broomrape). Plants parasitizing on roots cause significant damage in crops before emergence and thus lead to high economical losses. Therefore handpulling or mechanical weeding may prevent the parasite from seed setting, however, these measures come too late to prevent crop losses. The longevity of the seeds of parasitic species is relatively high. Therefore crop rotation or fallow is often not practical since intervals between the cultivation of susceptible crops have to be 5 to 10 years depending on the specific system. Conferring resistance against parasitic weeds on crop plants through selection or genetic modification is only partly successful as parasitic weeds are able to adopt to such changes quickly (Höniges, A., Wegmann, K.* and Ardelean, A. HELIA, 31, Nr. 49, p.p. 1-12, (2008).

Plant growth regulators (PGRs) interact with the hormonal system of the treated plants and regulate the growth of a plant or parts of a plant. They affect developmental processes and differentiation in plants at low dosages without having a nutritive value or being phytotoxic. More specifically, various PGRs can, for example, reduce plant height, stimulate seed germination, induce flowering, darken leaf coloring, minimize lodging of cereals, change the rate of plant growth and modify the timing and efficiency of flowering, fruit formation, ripening, fruit drop, defoliation or quality traits.

There are several different classes of plant growth regulators. Known classes include azoles (such as uniconazole and paclobutrazol), cyclohexane carboxylates (such as trinexapac, trinexapac-ethyl, prohexadione and prohexadione-calcium), pyrimidinyl carbinols (such as flurprimidol and ancyrnidol), quarternary ammoniums (such as chlormequat-chloride and mepiquat-chloride) and sulphonyl-amino phenyl-acetamides (such as mefluidide).

Plant growth regulators operate by various modes of action (W. Rademacher, *Ann. Rev. Plant Physiol. Plant Biol.* 2000, 51, 501-531). Prohexadione, prohexadione-calcium, trinexapac and trinexapac-ethyl act as inhibitors of aminocyclopropane carboxylic acid (ACC) oxidase and hence inhibit the biosynthesis of ethylene.

Ethylene serves as a hormone in plants Z. Lin et al., "Recent advances in ethylene research", *J. Exp. Bot.*, 2009, 60, 3311-3336). It acts at trace levels within the plant by stimulating or regulating the ripening of fruit as well as senescence of vegetative tissues. Ethylene biosynthesis can be induced or inhibited by plant growth regulators (S. F. Yang et al. "Ethylene biosynthesis and its regulation in higher plants". *Ann. Rev. Plant Physiol.* 1984, 35, 155-89). As opposed to inhibitors of ethylene biosynthesis, inhibitors of ethylene perception include compounds that have a similar shape to ethylene, but do not elicit the ethylene response. One example of an ethylene perception inhibitor is 1-methylcyclopropene (1-MCP). WO 2008124431 (A1) relates to synergistic mixtures comprising 1-MCP for improving yield, health and/or vigor of plants.

It has been reported in EP 0123001 (A1) that prohexadione-calcium induces sunflower resistance against infection with the root parasitic weed *Orobanche cumana* (Z. W. Fan et al., *Weed Research* 2007, 4Z 34-43).

US 2011/0028324 discloses a method of controlling weeds using mixtures of non-selective herbicides and plant growth regulators. It also relates to mixtures of non-selective herbicides and plant growth regulators and compositions comprising them.

Acetolactate synthase (ALS) inhibitors are herbicidally active compounds, which inhibit the branched chain amino acid biosynthesis. They belong to the group B of the HRAC classification system. WO 2003/012115 (A2) and WO 2008/124431 (A1) relate to herbicide-resistant sunflower plants and methods for controlling broomrape comprising applying, inter alia, acetolactate synthase inhibitors such as imidazolinones or sulfonylureas. EP 1088480 (A1) relates to the selective use of imazetapyr in varieties of sunflowers that are resistant or tolerant to said herbicide for the control of *Orobanche cernua* or *Orobanche cumana*. US 2005/44587 (A1) relates to sunflower lines and hybrids that are tolerant to sulfonylurea herbicides and to a method for selective control of undesired vegetation, including parasitic weeds, preferably *Orobanche* spp., by applying sulfonylurea herbicides to sulfonylurea-tolerant sunflower crops.

As to the given mechanisms of action and classification of the active substances, see e.g. "HRAC, Classification of Herbicides According to Mode of Action".

There are only few selective herbicides that control root parasitic weeds season long while they are still underground. In order to prevent damage to the host plant a herbicide that can translocate within the host plant must be applied in concentrations which are non-toxic to the host. For this reason there is a strong need in the agrochemical industry to provide new methods and chemical compositions for the efficient control of root parasitic weeds like, for example, *Orobanche* spp. and *Striga* spp.

It is an objective of the present invention to provide herbicidal mixtures or compositions, which are highly active against parasitic weeds, especially root parasitic weeds. At the same time, the compositions should have good compatibility with useful plants. In addition, the compositions according to the invention should have a broad spectrum of activity and ultimately help increase the yield of the crop plant.

It was found that herbicidally active mixtures or compositions comprising one, two or three acetolactate synthase (ALS) inhibitor(s) and one, two or three plant growth regulator(s) (PGR) which act as ethylene modulators are very useful for controlling parasitic weeds.

Surprisingly, the mixtures and compositions according to the invention have better herbicidal activity, i.e. better activity against parasitic weeds, than would have been expected based on the herbicidal activity observed for the individual components. In addition to the improved herbicidal activity the mixtures and compositions according to the present invention also provide for significantly improved yields of the crop plant.

The herbicidal activity to be expected for mixtures and compositions based on the individual component can be calculated using Colby's formula (see below). If the observed activity exceeds the expected additive activity of the individual components, this effect is referred to as "synergism".

The present invention relates to a method for controlling parasitic weeds, comprising applying to the host plant, the weeds and/or their habitat a herbicidal mixture comprising components
A) one, two or three herbicidally active compound(s) from the group of acetolactate synthase (ALS) inhibitors, and
B) one, two or three plant growth regulator(s) (PGR) which act as ethylene modulators selected from L-2-amino-4-alkoxy-trans-3-butenoic acid, L-canaline, Co++ or Ni++ ions in plant-available forms, n-propyl gallate, n-octyl gallate, n-dodecyl gallate, putrescine, spermine or spermidine, α-aminoisobutyric acid, L-aminocyclopropene-1-carboxylic acid, salicylic acid, acibenzolar-S-methyl, prohexadione, prohexadione-calcium, trinexapac, trinexapac-ethyl, paclobutrazole, metconazole, uniconazole, 1-methylcyclopropene, 2,5-norbornadiene, 3-amino-1,2,4-triazole or Ag++ ions including their agriculturally acceptable salts or derivatives,
in a synergistically effective amount or a composition comprising said mixture.

In the method according to the invention, the mixtures or compositions comprising said mixtures are preferably applied in a synergistically effective amount, which is defined by a weight ratio of A) to B) from 1:300 to 300:1, preferably from 1:100 to 100:1, preferably from 1:20 to 20:1, preferably from 1:3 to 3:1, preferably from 1:2 to 2:1 and also preferably 1:1.

According to one embodiment, the inventive method comprises the application of herbicidal mixtures comprising components A) and B) and as a further ingredient a herbicidal, fungicidal or insecticidal component C).

Furthermore the present invention also relates to mixtures comprising components
A) one, two or three herbicidally active compounds selected from imazamox, imazapyr, imazaquin, imazamethabenz-methyl, tribenuron-methyl, flupyrsulfuron, mesosulfuron, imazasulfuron or foramsulfuron including their agriculturally acceptable salts or derivatives, and
B) one, two or three plant growth regulator(s) (PGR) selected from prohexadione, prohexadione-calcium, trinexapac or trinexapac-ethyl including their agriculturally acceptable salts or derivatives.

Preferably the mixtures comprise components A) and B) in a synergistically effective amount, which is defined by a weight ratio of A) to B) from 1:300 to 300:1, preferably from 1:100 to 100:1, preferably from 1:20 to 20:1, preferably from 1:3 to 3:1, preferably from 1:2 to 2:1 and also preferably 1:1.

According to one embodiment of the invention the mixture comprises as a further ingredient a fungicidal, herbicidal or insecticidal component C).

The term mixture herein relates to combinations of components A), B) and, optionally, C), i.e. active ingredients, which can be applied separately within a time frame that allows simultaneous action of the active ingredients on the plants, preferably within a time-frame of eight weeks, in particular at most 7 days, more particular at most 1 day.

Examples of ALS inhibitors, or components A), which can be used according to the present invention are sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron; imidazolinones such as imazamethabenz, imazamethabenz-methyl, imazamox, imazapic, imazapyr, imazaquin and imazethapyr; triazolopyrimidine herbicides and sulfonanilides such as cloransulam, cloransulam-methyl, diclosulam, flumetsulam, florasulam, metosulam, penoxsulam, pyrimisulfan and pyroxsulam; pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl] amino]-benzoic acid-1-methylethyl ester (CAS 420138-41-6), 4-[[[2-[(4,6-dimethoxy-2-pyrimidinyl)oxy]phenyl] methyl]amino]-benzoic acid propyl ester (CAS 420138-40-5), N-(4-bromophenyl)-2-[(4,6-dimethoxy-2-pyrimidinyl) oxy]benzenemethanamine (CAS 420138-01-8); sulfonylaminocarbonyl-triazolinone herbicides such as flucarbazone, flucarbazone-sodium, propoxycarbazone, propoxycarbazone-sodium, thiencarbazone and thiencarbazone-methyl and triafamone.

Examples of PGRs that act as ethylene modulators, herein referred to as components B), which can be used according to the present invention, are ethylene biosynthesis inhibitors, which inhibit the conversion of S-adenosyl-L-methionine into 1-aminocyclopropane-1-carboxylic acid (ACC), such as derivatives of vinylglycine, for example L-2-amino-4-alkoxy-trans-3-butenoic acid), hydroxylamines, for example L-canaline and their structural analogs, for example corresponding oxime ether derivatives, ethylene biosynthesis inhibitors which block the conversion of ACC into ethylene, selected from the group consisting of Co++ or Ni++ ions in plant-available forms or phenolic radical scavengers such as n-propyl gallate, n-octyl gallate, n-dodecyl gallate; polyamines, such as putrescine, spermine or spermidine, structural analogs of ACC, such as α-aminoisobutyric acid or L-aminocyclopropene-1-carboxylic acid; salicylic acid or acibenzolar-S-methyl and other structural analogs of ascorbic acid which act as inhibitors of ACC oxidase, such as prohexadione, prohexadione-calcium, trinexapac or trinexapac-ethyl; triazolyl compounds such as paclobutrazole, metconazole or uniconazole as inhibitors of cytochrome P-450-dependent monooxygenases whose main action is to block the biosynthesis of gibberellins or structural analogs of ethylene, for example 1-methylcyclopropene, 2,5-norbornadiene, 3-amino-1,2,4-triazole or Ag++ ions.

Examples for suitable components C) which can be used according to the present invention are, for example, strobilurin fungicides, for example, azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, 2-[2-(2,5-dimethyl-phenoxymethyl)-phenyl]-3-methoxy-acrylic acid methyl ester and 2-(2-(3-(2,6-di-chlorophenyl)-1-methyl-allylideneaminooxymethyl)-phenyl)-2-methoxy-imino-N-methyl-acetamide; or azole fungicides such as tebuconazole, metconazole, prothioconazole, difenoconazole, paclobutrazole, flusilazole, cyproconazole, propiconazole, fluquinazole; or succinate dehydrogenase inhibitors such as boscalid, bixafen, fluopyram, penthiopyrad isopyrazam, fluxapyroxad; or carbendazim, thiophanatemethyl, iprodione, chlorothalonil, mancozeb, procymidone, vinclozolin, famoxadone, triadimenol, fenpropimorph, cymoxanil, prochloraz; or herbicides selected from acetochlor, aclonifen, cycloxydim, tepraloxydim, clethodim, fenoxyaprop, propaquizafop, quizalafop, haloxyfop, pendimethalin, clomazone, metazachlor, Metolachlor, quinmerac, dimethenamid, ethametsulfuron, napropamide, pethoxamide, glyphosate, gluphosinate, sulfentrazone, carfentrazone, trifluralin, flurochloridone, oxadiazone, linuron.

The active components A), B) and C) that are listed above are known in the art, see, for example, The Alanwood Compendium of Pesticide Common Names; Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998.

In the context of the present invention the following synergistic mixtures as well as the application of said mixtures in the methods according to the invention are particularly preferred. The preferred embodiments of the invention mentioned hereinafter are preferred either independently from each other or in combination with one another.

Among these, a preferred embodiment of the invention relates to mixtures comprising as component A) an imidazolinone herbicide or a sulfonylurea herbicide or mixtures thereof.

According to a preferred embodiment of the invention component A) is a compound selected from the group of imidazolinones such as imazamethabenz-methyl, imazamox, imazapic, imazapyr, imazaquin and imazethapyr.

According to a preferred embodiment of the invention component A) is a compound selected from the group of imidazolinones consisting of imazamox, imazapyr, imazaquin, imazamethabenz-methyl or mixtures thereof.

According to a preferred embodiment of the invention component A) is a compound selected from the group of imidazolinones consisting of imazamox, imazapyr and imazethapyr or mixtures thereof.

According to a preferred embodiment of the invention component A) is a compound selected from the group of imidazolinones consisting of imazamox and imazapyr or mixtures thereof.

According to a preferred embodiment of the invention component A) is imazamox.

According to a preferred embodiment of the invention component A) is a sulfonylurea herbicide.

According to a preferred embodiment of the invention component A) is a compound selected from the group of sulfonylureas such as tribenuron-methyl, flupyrsulfuron, thifensulfuron-methyl, mesosulfuron, imazasulfuron, foramsulfuron, metsulfuron and ethametsulfuron or mixtures thereof.

According to a preferred embodiment of the invention component A) is a compound selected from the group of sulfonylureas consisting of tribenuron-methyl, flupyrsulfuron, mesosulfuron, imazasulfuron, foramsulfuron or mixtures thereof.

According to a preferred embodiment of the invention component A) is imazamox, imazapyr or tribenuron-methyl or mixtures thereof.

According to a preferred embodiment of the invention component A) is imazamox or tribenuron-methyl or mixtures thereof.

According to a preferred embodiment of the invention component A) is ethametsulfuron.

According to a preferred embodiment of the invention component A) is tribenuron-methyl.

According to a preferred embodiment of the invention component B) is prohexadione, prohexadione-calcium, trinexapac or trinexapac-ethyl or mixtures thereof.

According to a preferred embodiment of the invention component B) is prohexadione or prohexadione-calcium or mixtures thereof.

According to a preferred embodiment of the invention component B) is prohexadione-calcium.

According to a preferred embodiment of the invention component B) is trinexapac.

According to a preferred embodiment of the invention component B) is trinexapac-ethyl.

According to a preferred embodiment of the invention component C) is a fungicidal compound selected from the group of strobilurins such as dimoxystrobin, pyraclostrobin, azoxystrobin, trifloxystrobin, kresoxim-methyl or azole fungicides such as tebuconazole, metconazole, prothioconazole, difenoconazole, paclobutrazole, flusilazole, cyproconazole, propiconazole, fluquinazole; or succinate dehydrogenase inhibitors such as boscalid, bixafen, fluopyram, penthiopyrad isopyrazam, fluxapyroxad; or carbendazim, thiophanatemethyl, iprodione, chlorothalonil, mancozeb, procymidone, vinclozolin, famoxadone, triadimenol, fenpropimorph, cymoxanil, prochloraz.

According to a preferred embodiment of the invention component C) is a fungicidal compound selected from the group of strobilurins.

According to a preferred embodiment of the invention component C) is a compound selected from the group of pyraclostrobin and kresoxim-methyl.

According to a particularly preferred embodiment of the invention component C) is pyraclostrobin.

According to a preferred embodiment of the invention component C) is a herbicidal compound such as acetochlor, aclonifen, cycloxydim, tepraloxydim, clethodim, fenoxyaprop, propaquizafop, quizalafop, haloxyfop, pendimethalin, clomazone, metazachlor, Metolachlor, quinmerac, dimethenamid, ethametsulfuron, napropamide, pethoxamide, glyphosate, gluphosinate, sulfentrazone, carfentrazone, trifluralin, flurochloridone, oxadiazone, linuron.

If the components A) and/or B) and/or C) are capable of forming geometrical isomers, for example E/Z isomers, both the pure isomers and mixtures thereof may be used in the compositions according to the invention. If the components A) and/or B) and/or C) have one or more centers of chirality and are thus present as enantiomers or diastereomers, both the pure enantiomers and diastereomers and mixtures thereof may be used in the compositions according to the invention.

If the components A) and/or B) and/or C) have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, hydroxy-$C_1$-$C_4$-alkoxy-$C_1$-$C_4$-alkyl, phenyl or benzyl, preferably ammonium or mono-$C_1$-$C_4$-alkyl, tri-$C_1$-$C_4$-alkyl, tetra-$C_1$-$C_4$-alkylammonium that can be substituted by hydroxy or phenyl, for example, methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyeth-1-oxy)eth-1-ylammonium, di(2-hydroxyeth-1-yl)ammonium, benzyltrimethylammonium, benzyltriethylammonium, furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Active components A) and/or B) and/or C) having a carboxyl group can be employed in the form of the acid, in the form of an agriculturally suitable salt as mentioned above or else in the form of an agriculturally acceptable derivative in the compositions according to the invention, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters and also as thioesters, for example as $C_1$-$C_{10}$-alkylthio esters. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl) or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the methoxyethyl, ethoxyethyl or butoxyethyl ester. An example of a straight-chain or branched $C_1$-$C_{10}$-alkylthio ester is the ethylthio ester.

In the context of the present invention the following mixtures as well as the application of said mixtures in the methods according to the invention are particularly preferred.

Mixtures comprising exactly one ALS inhibitor.
Mixtures comprising exactly two ALS inhibitors.
Mixtures comprising exactly three ALS inhibitors.
Mixtures comprising exactly one PGR.
Mixtures comprising exactly two PGRs.
Mixtures comprising exactly one ALS inhibitor and exactly one PGR.
Mixtures comprising exactly two ALS inhibitors and exactly one PGR.
Mixtures comprising exactly three ALS inhibitors and exactly one PGR.
Mixtures comprising exactly one ALS inhibitor and exactly two PGRs.
Mixtures comprising exactly two ALS inhibitors and exactly two PGRs.
Mixtures comprising exactly three ALS inhibitors and exactly two PGRs.

Further preferred embodiments relate to ternary mixtures which correspond to the binary mixtures mentioned above and additionally comprise a component C).

Here and below, the term "binary mixtures" includes mixtures comprising 1, 2 or 3 active herbicidal components A) and either 1, 2 or 3, PGR components B). Correspondingly, the term "ternary compositions" includes mixtures comprising 1, 2 or 3, active components A), one or more, for example 1, 2 or 3, components B) and one or more, for example 1, 2 or 3 components C).

In binary mixtures comprising 1, 2 or 3 herbicidal components A) and 1, 2 or 3 components B), the weight ratio of the active compounds A:B is generally in the range from 1:300 to 300:1, in particular in the range from 1:100 to 100:1 and preferably in the range from 1:3 to 3:1, in particular in the range from 1:2 to 2:1 and even more preferably 1:1.

In ternary mixtures the relative proportions by weight of the components A:B are generally in the range from 1:300 to 300:1, preferably in the range from 1:100 to 100:1 and preferably in the range from 1:3 to 3:1, in particular in the range from 1:2 to 2:1 and even more preferably 1:1 The weight ratio of the components A:C is generally in the range from 1:3000 to 3000:1, preferably in the range from 1:1000 to 1000:1, in particular in the range from 1:100 to 100:1 and particularly preferably in the range from 1:20 to 20:1 and even more preferably in the range from 1:3 to 3:1. The weight ratio of the components B:C is generally in the range from 1:1000 to 1000:1, preferably in the range from 1:500 to 500:1, in particular in the range from 1:250 to 250:1 and particularly preferably in the range from 1:75 to 75:1 and even more preferably in the range from 1:20 to 20:1. The weight ratio of components A+B to component C is preferably in the range from 1:1000 to 1000:1, in particular in the range from 1:100 to 100:1 and particularly preferably in the range from 1:5 to 5:1 and even more preferably in the range from 1:3 to 3:1.

Particularly preferred components A) in the methods of the present invention are listed in table I.

TABLE I

| | Component A |
|---|---|
| A.1 | amidosulfuron |
| A.2 | azimsulfuron |
| A.3 | bensulfuron |
| A.4 | bensulfuron-methyl |
| A.5 | chlorimuron |
| A.6 | chlorimuron-ethyl |
| A.7 | chlorsulfuron |
| A.8 | cinosulfuron |
| A.9 | cyclosulfamuron |
| A.10 | ethametsulfuron |
| A.11 | ethametsulfuron-methyl |
| A.12 | ethoxysulfuron |
| A.13 | flazasulfuron |
| A.14 | flucetosulfuron |

TABLE I-continued

| | Component A |
|---|---|
| A.15 | flupyrsulfuron |
| A.16 | flupyrsulfuron-methyl-sodium |
| A.17 | foramsulfuron |
| A.18 | halosulfuron |
| A.19 | halosulfuron-methyl |
| A.20 | imazosulfuron |
| A.21 | iodosulfuron |
| A.22 | iodosulfuron-methyl-sodium |
| A.23 | mesosulfuron |
| A.24 | metazosulfuron |
| A.25 | metsulfuron |
| A.26 | metsulfuron-methyl |
| A.27 | nicosulfuron |
| A.28 | orthosulfamuron |
| A.29 | oxasulfuron |
| A.30 | primisulfuron |
| A.31 | primisulfuron-methyl |
| A.32 | propyrisulfuron |
| A.33 | prosulfuron |
| A.34 | pyrazosulfuron |
| A.35 | pyrazosulfuron-ethyl |
| A.36 | rimsulfuron |
| A.37 | sulfometuron |
| A.38 | sulfometuron-methyl |
| A.39 | sulfosulfuron |
| A.40 | thifensulfuron |
| A.41 | thifensulfuron-methyl |
| A.42 | triasulfuron |
| A.43 | tribenuron |
| A.44 | tribenuron-methyl |
| A.45 | trifloxysulfuron |
| A.46 | triflusulfuron |
| A.47 | triflusulfuron-methyl |
| A.48 | tritosulfuron |
| A.49 | imazamethabenz |
| A.50 | imazamethabenz-methyl |
| A.51 | imazamox |
| A.52 | imazapic |
| A.53 | imazapyr |
| A.54 | imazaquin |
| A.55 | imazethapyr |
| A.56 | cloransulam |
| A.57 | cloransulam-methyl |
| A.58 | diclosulam |
| A.59 | flumetsulam |
| A.60 | florasulam |
| A.61 | metosulam |
| A.62 | penoxsulam |
| A.63 | pyrimisulfan |
| A.64 | pyroxsulam |
| A.65 | bispyribac |
| A.66 | bispyribac-sodium |
| A.67 | pyribenzoxim |
| A.68 | pyriftalid |
| A.69 | pyriminobac |
| A.70 | pyriminobac-methyl |
| A.71 | pyrithiobac |
| A.72 | pyrithiobac-sodium |
| A.73 | 4-[[[2-[(4,6-dimethoxy-2-pyrimidinyl)oxy]phenyl]methyl]amino]-benzoic acid-1-methyl-ethyl ester (CAS 420138-41-6) |
| A.74 | 4-[[[2-[(4,6-dimethoxy-2-pyrimidinyl)oxy]phenyl]-methyl]amino]-benzoic acid propyl ester (CAS 420138-40-5) |
| A.75 | N-(4-bromophenyl)-2-[(4,6-dimethoxy-2-pyrimidinyl)oxy]benzenemethanamine (CAS 420138-01-8) |
| A.76 | flucarbazone |
| A.77 | flucarbazone-sodium |
| A.78 | propoxycarbazone |
| A.79 | propoxycarbazone-sodium |

TABLE I-continued

| | Component A |
|---|---|
| A.80 | thiencarbazone |
| A.81 | thiencarbazone-methyl |
| A.82 | triafamone |

Particularly preferred components B) in the methods of the present invention are listed in table II.

TABLE II

| | Component B |
|---|---|
| B.1 | L-2-amino-4-alkoxy-trans-3-butenoic acid |
| B.2 | L-canaline |
| B.3 | Co++ ions |
| B.4 | Ni++ ions |
| B.5 | n-propyl gallate |
| B.6 | n-octyl gallate |
| B.7 | n-dodecyl gallate |
| B.8 | putrescine |
| B.9 | spermine |
| B.10 | spermidine |
| B.11 | α-aminoisobutyric acid |
| B.12 | L-aminocyclopropene-1-carboxylic acid |
| B.13 | prohexadione |
| B.14 | prohexadione-calcium |
| B.15 | trinexapac |
| B.16 | trinexapac-ethyl |
| B.17 | paclobutrazole |
| B.18 | uniconazole |

The methods applying mixtures compiled in the following tables 1a to 18a are particularly preferred embodiments of the present invention.

Table 1a

A method according to the invention applying a mixture comprising components A) and B), wherein component B) is L-2-amino-4-alkoxy-trans-3-butenoic acid (B.1) and component A) corresponds to one component A) as identified in each line of table I respectively (Mixtures B.1A.1 to B.1A.82)

Table 2a

A method according to the invention applying a mixture comprising components A) and B), wherein component B) is L-canaline (B.2) and component A) corresponds to one component A) as identified in each line of table I respectively (Mixtures B.2A.1 to B.2A.82)

Table 3a

A method according to the invention applying a mixture comprising components A) and B), wherein component B) is Co++ ions (B.3) in plant-available form and component A) corresponds to one component A) as identified in each line of table I respectively (Mixtures B.3A.1 to B.3A.82)

Table 4a

A method according to the invention applying a mixture comprising components A) and B), wherein component B) is Ni++ ions (B.4) in plant-available form and component A) corresponds to one component A) as identified in each line of table I respectively (Mixtures B.4A.1 to B.4A.82)

Table 5a

A method according to the invention applying a mixture comprising components A) and B), wherein component B) is n-propyl gallate (B.5) and component A) corresponds to one component A) as identified in each line of table I respectively (Mixtures B.5A.1 to B.5A.82)

Table 6a
A method according to the invention applying a mixture comprising components A) and B), wherein component B) is n-octyl gallate (B.6) and component A) corresponds to one component A) as identified in each line of table I respectively (Mixtures B.6A.1 to B.6A.82)

Table 7a
A method according to the invention applying a mixture comprising components A) and B), wherein component B) is n-dodecyl gallate (B.7) and component A) corresponds to one component A) as identified in each line of table I respectively (Mixtures B.7A.1 to B.7A.82)

Table 8a
A method according to the invention applying a mixture comprising components A) and B), wherein component B) is putrescine (B.8) and component A) corresponds to one component A) as identified in each line of table I respectively (Mixtures B.8A.1 to B.8A.82)

Table 9a
A method according to the invention applying a mixture comprising components A) and B), wherein component B) is spermine (B.9) and component A) corresponds to one component A) as identified in each line of table I respectively (Mixtures B.9A.1 to B.9A.82)

Table 10a
A method according to the invention applying a mixture comprising components A) and B), wherein component B) is spermidine (B.10) and component A) corresponds to one component A) as identified in each line of table I respectively (Mixtures B.10A.1 to B.10A.82)

Table 11a
A method according to the invention applying a mixture comprising components A) and B), wherein component B) is α-aminoisobutyric acid (B.11) and component A) corresponds to one component A) as identified in each line of table I respectively (Mixtures B.11A.1 to B.11A.82)

Table 12a
A method according to the invention applying a mixture comprising components A) and B), wherein component B) is L-aminocyclopropene-1-carboxylic acid (B.12) and component A) corresponds to one component A) as identified in each line of table I respectively (Mixtures B.12A.1 to B.12A.82)

Table 13a
A method according to the invention applying a mixture comprising components A) and B), wherein component B) is prohexadione (B.13) and component A) corresponds to one component A) as identified in each line of table I respectively (Mixtures B.13A.1 to B.13A.82)

Table 14a
A method according to the invention applying a mixture comprising components A) and B), wherein component B) is prohexadione-calcium (B.14) and component A) corresponds to one component A) as identified in each line of table I respectively (Mixtures B.14A.1 to B.14A.82)

Table 15a
A method according to the invention applying a mixture comprising components A) and B), wherein component B) is trinexapac (B.15) and component A) corresponds to one component A) as identified in each line of table I respectively (Mixtures B.15A.1 to B.15A.82)

Table 16a
A method according to the invention applying a mixture comprising components A) and B), wherein component B) is trinexapac-ethyl (B.16) and component A) corresponds to one component A) as identified in each line of table I respectively (Mixtures B.16A.1 to B.16A.82)

Table 17a
A method according to the invention applying a mixture comprising components A) and B), wherein component B) is paclobutrazole (B.17) and component A) corresponds to one component A) as identified in each line of table I respectively (Mixtures B.17A.1 to B.17A.82)

Table 18a
A method according to the invention applying a mixture comprising components A) and B), wherein component B) is uniconazole (B.18) and component A) corresponds to one component A) as identified in each line of table I respectively (Mixtures B.18A.1 to B.18A.82)

Accordingly a mixture of, for example, imazamox and prohexadione-calcium is denominated as mixture B14.A51 or, for example, bensulfuron-methyl and trinexapac-ethyl is denominated as mixture B15.A4.

Particularly preferred embodiments of the present invention relate to methods comprising applying mixtures according to table III.

TABLE III

| | Component A | Component B |
|---|---|---|
| C.1 | imazamethabenz | prohexadione-calcium |
| C.2 | imazamethabenz-methyl | prohexadione-calcium |
| C.3 | imazamox | prohexadione-calcium |
| C.4 | imazapic | prohexadione-calcium |
| C.5 | imazapyr | prohexadione-calcium |
| C.6 | imazaquin | prohexadione-calcium |
| C.7 | imazethapyr | prohexadione-calcium |
| C.8 | imazamethabenz | prohexadione |
| C.9 | imazamethabenz-methyl | prohexadione |
| C.10 | imazamox | prohexadione |
| C.11 | imazapic | prohexadione |
| C.12 | imazapyr | prohexadione |
| C.13 | imazaquin | prohexadione |
| C.14 | imazethapyr | prohexadione |
| C.15 | imazamethabenz | trinexapac |
| C.16 | imazamethabenz-methyl | trinexapac |
| C.17 | imazamox | trinexapac |
| C.18 | imazapic | trinexapac |
| C.19 | imazapyr | trinexapac |
| C.20 | imazaquin | trinexapac |
| C.21 | imazethapyr | trinexapac |
| C.22 | imazamethabenz | trinexapac-ethyl |
| C.23 | imazamethabenz-methyl | trinexapac-ethyl |
| C.24 | imazamox | trinexapac-ethyl |
| C.25 | imazapic | trinexapac-ethyl |
| C.26 | imazapyr | trinexapac-ethyl |
| C.27 | imazaquin | trinexapac-ethyl |
| C.28 | imazethapyr | trinexapac-ethyl |
| C.29 | tribenuron-methyl | prohexadione-calcium |
| C.30 | flupyrsulfuron | prohexadione-calcium |
| C.31 | thifensulfuron-methyl | prohexadione-calcium |
| C.32 | mesosulfuron | prohexadione-calcium |
| C.33 | imazasulfuron | prohexadione-calcium |
| C.34 | foramsulfuron | prohexadione-calcium |
| C.35 | metsulfuron | prohexadione-calcium |
| C.36 | ethametsulfuron | prohexadione-calcium |
| C.37 | tribenuron-methyl | trinexapac |
| C.38 | flupyrsulfuron | trinexapac |
| C.39 | thifensulfuron-methyl | trinexapac |
| C.40 | mesosulfuron | trinexapac |
| C.41 | imazasulfuron | trinexapac |
| C.42 | foramsulfuron | trinexapac |
| C.43 | metsulfuron | trinexapac |
| C.44 | ethametsulfuron | trinexapac |
| C.45 | tribenuron-methyl | trinexapac-ethyl |
| C.46 | flupyrsulfuron | trinexapac-ethyl |
| C.47 | thifensulfuron-methyl | trinexapac-ethyl |
| C.48 | mesosulfuron | trinexapac-ethyl |
| C.49 | imazasulfuron | trinexapac-ethyl |
| C.50 | foramsulfuron | trinexapac-ethyl |

TABLE III-continued

| | Component A | Component B |
|---|---|---|
| C.51 | metsulfuron | trinexapac-ethyl |
| C.52 | ethametsulfuron | trinexapac-ethyl |

Further particularly preferred embodiments of the present invention relate to methods comprising applying mixtures as compiled in tables 1a to 18a each in combination with pyraclostrobin.

Further particularly preferred embodiments of the present invention relate to methods comprising applying mixtures as compiled in tables 1a to 18a each in combination with kresoxim-methyl.

Further particularly preferred embodiments of the present invention relate to methods comprising applying mixtures as compiled in table III (C.1 to C.52) each in combination with pyraclostrobin.

Further particularly preferred embodiments of the present invention relate to methods comprising applying mixtures as compiled in table III (C.1 to C.52) each in combination with kresoxim-methyl.

The mixtures according to the invention are suitable as herbicides. They are suitable as such or as an appropriately formulated composition. They act against broad-leafed weeds and grass weeds, particularly against *Orobanche* spp. and *Striga* spp., particularly *Orobanche* spp. in crops such as sunflower, oilseedrape, wheat, rice, corn, soybeans and cotton without causing any significant damage to the crop plants.

Another preferred embodiment of the invention relates to a method for controlling parasitic weeds in useful vegetation selected from the group of sunflower, oilseed rape, canola, soybeans, corn, peas, beans and alfalfa.

Another preferred embodiment of the invention relates to a method for improving the yield of the crop plant in useful vegetation selected from the group of sunflower, oilseed rape, canola, soybeans, corn, peas, beans and alfalfa.

Another preferred embodiment of the invention relates to a method for controlling parasitic weeds in sunflower and oilseed rape, particularly sunflower.

Another preferred embodiment of the invention relates to a method for improving the yield of the crop plant in sunflower and oilseed rape, particularly sunflower.

The components of the mixtures may be applied either simultaneously or sequentially or as premix. If administered sequentially, the components may be applied in any order and combination in a suitable time scale, for example, with up to 8 weeks between the time of applying the first component or combination and the time of applying the last component or combination. According to one embodiment the components are applied within 24 hours. More suitably, the components are applied within a few hours, preferably within one hour. In a preferred embodiment of the invention, the herbicide is applied first in case of sequential application. Preferably the components are applied simultaneously or in sequence. Particularly preferred application sequences D.1 to D.28 of components A), B) and, optionally, C) are listed below in table IV.

TABLE IV

| | 1st application | 2nd application | 3rd application |
|---|---|---|---|
| D.1 | A | B | |
| D.2 | A | B | C |
| D.3 | A | C | B |
| D.4 | A | B + C | |
| D.5 | B | A | |
| D.6 | B | A | C |
| D.7 | B | C | A |
| D.8 | B | A + C | |
| D.9 | C | A | B |
| D.10 | C | B | A |
| D.11 | C | A + B | A + B |
| D.12 | C | A + B | |
| D.13 | A + C | B | |
| D.14 | B + C | A | |
| D.15 | B + C | A + B | |
| D.16 | A + B | | |
| D.17 | A + B | C | |
| D.18 | A + B | A + B | |
| D.19 | A + B | A + B | A + B |
| D.20 | A + B | A + B | C |
| D.21 | A + B | A + B | B + C |
| D.22 | A + B | C | C |
| D.23 | A + B | B + C | |
| D.24 | A + B + C | | |
| D.25 | A + B + C | A + B + C | |
| D.26 | A + B + C | A + B + C | A + B + C |
| D.27 | A + C | B | B |
| D.28 | A + C | A + C | B |

Further preferred embodiments of the present invention relate to a method for controlling parasitic weeds, comprising applying to the host plant, the weeds and/or their habitat, in application sequences defined in rows D.1 to D.28 of table IV above, herbicidal mixtures as described in the context of the present invention. Tables 1d to 28d represent particularly preferred embodiments:

Table 1d
    A method for controlling parasitic weeds, comprising applying to the host plant, the weeds and/or their habitat, in an application sequence as defined in row D.1 of table IV above, herbicidal mixtures that comprise components as compiled in tables 1a to 18a.

Table 2d
    A method for controlling parasitic weeds, comprising applying to the host plant, the weeds and/or their habitat, in an application sequence as defined in row D.2 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 3d
    A method for controlling parasitic weeds, comprising applying to the host plant, the weeds and/or their habitat, in an application sequence as defined in row D.3 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 4d
    A method for controlling parasitic weeds, comprising applying to the host plant, the weeds and/or their habitat, in an application sequence as defined in row D.4 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 5d
A method for controlling parasitic weeds, comprising applying to the host plant, the weeds and/or their habitat, in an application sequence as defined in row D.5 of table IV above, herbicidal mixtures that comprise components as compiled in tables 1a to 18a.

Table 6d
A method for controlling parasitic weeds, comprising applying to the host plant, weeds and/or their habitat, in an application sequence as defined in row D.6 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 7d
A method for controlling parasitic weeds, comprising applying to the host plant, the weeds and/or their habitat, in an application sequence as defined in row D.7 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 8d
A method for controlling parasitic weeds, comprising applying to the host plant, weeds and/or their habitat, in an application sequence as defined in row D.8 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 9d
A method for controlling parasitic weeds, comprising applying to the host plant, the weeds and/or their habitat, in an application sequence as defined in row D.9 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 10d
A method for controlling parasitic weeds, comprising applying to the host plant, the weeds and/or their habitat, in an application sequence as defined in row D.10 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 11d
A method for controlling parasitic weeds, comprising applying to the host plant, weeds and/or their habitat, in an application sequence as defined in row D.11 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 12d
A method for controlling parasitic weeds, comprising applying to the host plant, weeds and/or their habitat, in an application sequence as defined in row D.12 of table IV above, herbicidal mixtures that comprise components as compiled in tables 1a to 18a.

Table 13d
A method for controlling parasitic weeds, comprising applying to the host plant, weeds and/or their habitat, in an application sequence as defined in row D.13 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 14d
A method for controlling parasitic weeds, comprising applying to the host plant, weeds and/or their habitat, in an application sequence as defined in row D.14 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 15d
A method for controlling parasitic weeds, comprising applying to the host plant, weeds and/or their habitat, in an application sequence as defined in row D.15 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 16d
A method for controlling parasitic weeds, comprising applying to the host plant, weeds and/or their habitat, in an application sequence as defined in row D.16 of table IV above, herbicidal mixtures that comprise components as compiled in tables 1a to 18a.

Table 17d
A method for controlling parasitic weeds, comprising applying to the host plant, weeds and/or their habitat, in an application sequence as defined in row D.17 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 18d
A method for controlling parasitic weeds, comprising applying to the host plant, weeds and/or their habitat, in an application sequence as defined in row D.18 of table IV above, herbicidal mixtures that comprise components as compiled in tables 1a to 18a.

Table 19d
A method for controlling parasitic weeds, comprising applying to the host plant, weeds and/or their habitat, in an application sequence as defined in row D.19 of table IV above, herbicidal mixtures that comprise components as compiled in tables 1a to 18a.

Table 20d
A method for controlling parasitic weeds, comprising applying to the host plant, weeds and/or their habitat, in an application sequence as defined in row D.20 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 21d
A method for controlling parasitic weeds, comprising applying to the host plant, weeds and/or their habitat, in an application sequence as defined in row D.21 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 22d
A method for controlling parasitic weeds, comprising applying to the host plant, weeds and/or their habitat, in an application sequence as defined in row D.22 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 23d
A method for controlling parasitic weeds, comprising applying to the host plant, weeds and/or their habitat, in an application sequence as defined in row D.23 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 24d
A method for controlling parasitic weeds, comprising applying to the host plant, weeds and/or their habitat, in an application sequence as defined in row D.24 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 25d
A method for controlling parasitic weeds, comprising applying to the host plant, the weeds and/or their habitat, in an application sequence as defined in row D.25 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 26d
A method for controlling parasitic weeds, comprising applying to the host plant, the weeds and/or their habitat, in an application sequence as defined in row D.26 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 27d
A method for controlling parasitic weeds, comprising applying to the host plant, the weeds and/or their habitat, in an application sequence as defined in row D.27 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

Table 28d
A method for controlling parasitic weeds, comprising applying to the host plant, the weeds and/or their habitat, in an application sequence as defined in row D.28 of table IV above, herbicidal mixtures that comprise components as compiled in tables 1a to 18a in combination with pyraclostrobin or herbicidal mixtures that comprise components as compiled in tables 1a to 18a in combination with kresoxim-methyl.

The invention further relates to methods for improving the yield of the crop plant comprising applying herbicidal mixtures in application sequences as described in tables 1d to 28d.

If the components are administered simultaneously, they may be administered as a tank mix or as a pre-formulated mixture of all components or as a pre-formulated mixture of some components tank mixed with the remaining components.

The simultaneous or sequential application of components according to the invention can be done repeatedly. A preferred embodiment of the invention is a single application. Another preferred embodiment of the invention is a double application. Another preferred embodiment of the invention is a triple application. Another preferred embodiment of the invention is a quadruple application.

The mixtures and compositions according to the invention can also be used in genetically modified plants. The term "genetically modified plants" herein referred to are plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted post-translational modification of protein(s), oligo- or polypeptides. e. g., by inclusion therein of amino acid mutation(s) that permit, decrease, or promote glycosylation or polymer additions such as prenylation, acetylation farnesylation, or PEG moiety attachment.

Plants that have been modified by breeding, mutagenesis or genetic engineering, e.g. have been rendered tolerant to applications of specific classes of herbicides, such as auxinic herbicides such as dicamba or 2,4-D; bleacher herbicides such as 4-hydroxyphenylpyruvate dioxygenase (HPPD) inhibitors or phytoene desaturase (PDS) inhibitors; acetolactate synthase (ALS) inhibitors such as sulfonylureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetylCoA carboxylase (ACCase) inhibitors; or oxynil (i. e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxinic herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutagenesis and conventional methods of breeding, e. g., Clearfield® oil seed rape (summer rape or winter rape) or Clearfield® sunflower (BASF SE, Germany) being tolerant to imidazolinones, e. g., imazamox, or ExpressSun® sunflowers (DuPont, USA) or SURES-1 and SURES-2 (USDA-ARS, USA) being tolerant to sulfonyl ureas, e. g., tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as delta-endotoxins, e. g., CryIA(b), CryIA(c), CryIF, CryIF(a2), CryIIA(b), CryIIIA, CryIIIB(b1) or Cry9c; vegetative insecticidal proteins (VIP), e. g., VIP1, VIP2, VIP3 or VIP3A; insecticidal proteins of bacteria colonizing nematodes, e. g., *Photorhabdus* spp. or *Xenorhabdus* spp.; toxins produced by animals, such as scorpion toxins, arachnid toxins, wasp toxins, or other insect-specific neurotoxins; toxins produced by fungi, such as *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pre-toxins, hybrid proteins, truncated or otherwise modified proteins. Hybrid proteins are characterized by a new combination of protein domains, (see, e. g., WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g., in the publications mentioned above. These insecticidal proteins contained in the genetically modified plants impart to the plants producing these proteins tolerance to harmful pests from all taxonomic groups of arthropods, especially to beetles (*Coleoptera*), two-winged insects (*Diptera*), and moths (*Lepidoptera*) and to nematodes (*Nematoda*). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g., Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e. g., potato culti-vars, which express resistance genes acting against *Phytophthora infestans* derived from the Mexican wild potato, *Solanum bulbocastanum*) or T4-lyso-zym (e.g., potato cultivars capable of synthesizing these proteins with increased resistance against bacteria such as *Erwinia amylovora*). The methods for producing such genetically modified plants are generally known to the person skilled in the art and are described, e.g., in the publications mentioned above.

Furthermore, plants are also covered that are by the use of recombinant DNA techniques capable to synthesize one or more proteins to increase the productivity (e.g., bio-mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of ingredients or new ingredients, specifically to improve human or animal nutrition, e. g., oil crops that produce health-promoting long-chain omega-3 fatty acids or unsaturated omega-9 fatty acids (e. g., Nexera® rape, Dow Agro-Sciences, Canada).

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

The term seed comprises seed of all types, such as, for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

The components A), B) and C) according to the present invention, their N-oxides and salts can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International. The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

The invention relates in particular to herbicidally active mixtures comprising a component A) and component B) and, optionally, a component C), as defined above, and also, in case of compositions, at least one liquid and/or solid carrier and/or one or more surfactants and, if desired, one or more further auxiliaries customary for crop protection compositions.

The invention also relates to a mixture formulated as a 1-component composition comprising a component A) and a component B) and, optionally, a component C), and at least one solid or liquid carrier and/or one or more surfactants and, if desired, one or more further auxiliaries customary for crop protection compositions.

The invention also relates to a mixture formulated as a 2-component composition comprising a first component A), a solid or liquid carrier and/or one or more surfactants, and a second component B) and, optionally, a component C), a solid or liquid carrier and/or one or more surfactants, where additionally both components may also comprise further auxiliaries customary for crop protection compositions.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxilaries. Further examples are listed by Knowles, Adjuvants and additives, Agrow Reports DS256, T&F Informa UK, 2006, chapter 5.

In a preferred embodiment citric acid is used as an adjuvant.

In another preferred embodiment ammonium sulfate is used as an adjuvant.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

The components A), B) and, optionally, C) and the compositions of the invention can for example be formulated as follows:

i) Water-Soluble Concentrates (SL, LS)
10-60 wt % of active components A) and/or B) and, optionally, component C) according to the invention and 5-15 wt % wetting agent (e.g. alcohol alkoxylates) are dissolved in water and/or in a water-soluble solvent (e.g. alcohols) up to 100 wt %. The active substances dissolve upon dilution with water.

ii) Dispersible Concentrates (DC)
5-25 wt % of active components A) and/or B) and, optionally, component C) according to the invention and 1-10 wt % dispersant (e. g. polyvinylpyrrolidone) are dissolved in up to 100 wt % organic solvent (e.g. cyclohexanone). Dilution with water gives a dispersion.

iii) Emulsifiable Concentrates (EC)
15-70 wt % of active components A) and/or B) and, optionally, component C) according to the invention and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.

iv) Emulsions (EW, EO, ES)
5-40 wt % of active components A) and/or B) and, optionally, component C) according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)
In an agitated ball mill, 20-60 wt % of active components A) and/or B) and, optionally, component C) according to the invention are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active substances. For FS type composition up to 40 wt % binder (e.g. polyvinylalcohol) is added.

vi) Water-Dispersible Granules and Water-Soluble Granules (WG, SG)
50-80 wt % of active components A) and/or B) and, optionally, component C) according to the invention are ground finely with addition of up to 100 wt % dispersants and wetting agents (e.g. sodium lignosulfonate and alcohol ethoxylate) and prepared as water-dispersible or water-soluble granules by means of technical appliances (e. g. extrusion, spray tower, fluidized bed). Dilution with water gives a stable dispersion or solution of the active substances.

vii) Water-Dispersible Powders and Water-Soluble Powders (WP, SP, WS)
50-80 wt % of active components A) and/or B) and, optionally, component C) according to the invention are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substances.

viii) Gel (GW, GF)
In an agitated ball mill, 5-25 wt % of active components A) and/or B) and, optionally, component C) according to the invention are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substances.

ix) Microemulsion (ME)
5-20 wt % of active components A) and/or B) and, optionally, component C) according to the invention are added to 5-30 wt % organic solvent blend (e.g. fatty acid dimethylamide and cyclohexanone), 10-25 wt % surfactant blend (e.g. alkohol ethoxylate and arylphenol ethoxylate), and water up to 100%. This mixture is stirred for 1 h to produce spontaneously a thermodynamically stable microemulsion.

x) Microcapsules (CS)
An oil phase comprising 5-50 wt % of active components A) and/or B) and, optionally, component C) according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylene-diamine) results in the formation of a polyurea microcapsules. The monomers amount to 1-10 wt %. The wt % relate to the total CS composition.

xi) Dustable Powders (DP, DS)
1-10 wt % of active components A) and/or B) and, optionally, component C) according to the invention are ground finely and mixed intimately with up to 100 wt % solid carrier, e.g. finely divided kaolin.

xii) Granules (GR, FG)
0.5-30 wt % of active components A) and/or B) and, optionally, component C) according to the invention is ground finely and associated with up to 100 wt % solid carrier (e.g. silicate). Granulation is achieved by extrusion, spray-drying or the fluidized bed.

xiii) Ultra-Low Volume Liquids (UL)
1-50 wt % of active components A) and/or B) and, optionally, component C) according to the invention are dissolved in up to 100 wt % organic solvent, e.g. aromatic hydrocarbon.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100% (according to NMR spectrum).

Water-soluble concentrates (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required. When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per hectare.

The required application rates of components A) according to the present invention are generally in the range from 0.0005 kg/ha to 2.5 kg/ha and preferably in the range from 0.005 kg/ha to 2 kg/ha or 0.01 kg/ha to 1.5 kg/ha of active substance.

The required application rates of components B) according to the present invention are generally in the range from 0.0005 kg/ha to 2.5 kg/ha and preferably in the range from 0.005 kg/ha to 2 kg/ha or 0.01 kg/ha to 1.5 kg/ha of active substance.

The required application rates of components C) according to the present invention are generally in the range from 0.0005 kg/ha to 2.5 kg/ha and preferably in the range from 0.005 kg/ha to 2 kg/ha or 0.01 kg/ha to 1.5 kg/ha of active substance.

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1 and 1:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate. In a further embodiment, either individual components of the composition according to the invention or partially premixed components, e. g. comprising components A) and/or components B) and/or components C), may be mixed by the user in a spray tank and further auxiliaries and additives may be added, if appropriate.

In a further embodiment, either individual components of the composition according to the invention or partially premixed components, e. g. comprising components A) and/or components B) and/or components C), can be applied jointly (e.g. after tank mix) or consecutively.

Application of the herbicidal compositions according to the present invention can be done before, during and/or after, preferably during and/or after, the emergence or penetration to the host roots by the undesirable plants. The herbicidal compositions according to the present invention can be applied pre- or post-emergence or together with the seed of a crop plant. It is also possible to apply the compounds and compositions by applying to seeds of the host plant, pretreated with a composition of the invention. If the active components A and B and, if appropriate C, are less well tolerated by certain crop plants, application techniques may be used in which the herbicidal compositions are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

Moreover, it may be advantageous to apply the mixtures of the present invention on their own or jointly in combination with other crop protection agents, for example with agents for controlling pests or phytopathogenic fungi or bacteria or with groups of active compounds which regulate growth. Also of interest is the miscibility with mineral salt solutions which are employed for treating nutritional and trace element deficiencies. Non-phytotoxic oils and oil concentrates can also be added.

Examples

The herbicidal action of the mixtures according to the invention was demonstrated by the following field experiments:

Seeds of sunflower (*Helianthus annuus* L.) where sown as host test plants using small scale field experiment equipment. Host test plants were, uniform and homogeneous with respect to age, cultivar, and row spacing and distance in the row. Plot size 2.8 m×10 m—4 rows per plot. Test area was kept weed free of conventional weeds (monocotyledon and dicotyledonous weeds) by hand hoeing.

Natural infestations of parasitic weeds were present in the soil of the test areas.

Postemergence treatments where performed with up to 4 application timings regarding the growth stage of the host plant. Application timings are specified with M, N, O, and P and related to the following growth stages of the host test plants according to the BBCH-scale" Lancashire, P. D., H. Bleiholder, P. Langelüddecke, R. Stauss, T. van den Boom, E. Weber and A. Witzenberger, 1991: A uniform decimal code for growth stages of crops and weeds. Ann. appl. Biol. 119, 561-601", where M=2-4 true leafs (BBCH 12-14), N=6-7 true leafs (BBCH 16-17), O=8 to 10 leafs (BBCH 18-32) and P=10 leafs up to inflorescence emergence (BBCH 32-51).

Sequential application were performed with the solo active components and compared to the respective mixture. The respectively stated components A) and B) were used as commercially available formulations and, with addition of a solvent system, introduced into the spray medium used for applying the active composition. In the examples, the spray medium used was water. Imazamox was used as commercial aqueous solution (SL) having an active ingredient concentration of 40 g/liter (Pulsar 40 ®). Prohexadione-calcium was used as commercial water dispersible granules (WG) having an active ingredient concentration of 100 g/kg (Regalis®).

The test period extended over 1 to 4 month. During this time, the plants were tended, and their response to the individual treatments was carried out.

Evaluation was carried out using a scale from 0 to 100 to express activity (in %). 100% means no emergence of the parasitic plants, or complete destruction of at least the above-ground parts, and 0% means no damage or normal course of growth of the parasitic plants. Good herbicidal activity is given at values of at least 70, and very good herbicidal activity is given at values of at least 85.

In the examples below, using the method of S. R. Colby (1967) "Calculating synergistic and antagonistic responses of herbicide combinations", Weeds 15, p. 22ff., the value E, which is expected if the activity of the individual active compounds is only additive, was calculated.

$$E = X + Y - (X \cdot Y/100)$$

where

X=percent activity using active component A) at an application rate a;
Y=percent activity using active component B) at an application rate b;
E=expected activity (in %) by A)+B) at application rates a+b.

If the value found experimentally is higher than the value E calculated according to Colby, a synergistic effect is present.

The herbicidal activity of the tested compositions against *Orobanche cumana* (ORACE) according to the invention is compiled in table V.

| Weed | timing [BBCH growth stage] | g a.i./ha total Imazamox* | Prohexa-dione-Ca** | activity in % Imazamox | Prohex-adione-Ca | Imazamox + Prohex-adione-Ca | expected activity in % (Colby) | syner-gistic activity in % |
|---|---|---|---|---|---|---|---|---|
| ORACE | M, N, O, P | 50 | 100 | 69 | 2 | 100 | 70 | +30 |
| ORACE | M, O | 50 | 100 | 67 | 5 | 100 | 69 | +31 |
| ORACE | N, P | 50 | 100 | 68 | 8 | 100 | 71 | +29 |

*commercial product: Pulsar ®
**commercial product: Regalis ®

The delay of weed emergence and associated yield effects observed with the compositions according to the invention when tested against *Orobanche* sp. (ORASS) in sunflower is compiled in table VI. The number of *Orobanche* plants per host plant (imiazamox tolerant sunflower) and treatment were counted. The first visible emergence of *Orobanche* was assessed by counting the days from emergence of the sunflower till the first *Orobanche* appeared on the host. A later emergence is expressing a depression of the parasite as a result of the application of the active compounds. Yield of sunflower seeds was taken and compared to the control. A delay of emergence of *Orobanche* plants as well as a reduced number of *Orobanche* plants per host correlates with higher yield.

TABLE VI

| Trtm. | product | a.i. rate g/ha | timing [BBCH growth stage] | first visible emergence of orobanche (DAT***) | no. of orobanche plants per host plant | yield of sunflower seeds kg/ha |
|---|---|---|---|---|---|---|
| 1 | untreated | | | 22 | | 1127 |
| 2 | Imazamox* | 30 | 14-15 | 81 | 15 | 2055 |
| | Imazamox* | 20 | 16-18 | | | |
| 3 | Prohexadione-Ca** | 60 | 14-15 | 63 | 55 | 961 |
| | Prohexadione-Ca** | 40 | 16-18 | | | |
| 4 | Imazamox* | 30 | 14-15 | 88 | 11 | 2712 |
| | Prohexadione-Ca** | 60 | 14-15 | | | |
| | Imazamox* | 20 | 16-18 | | | |
| | Prohexadione-Ca** | 40 | 16-18 | | | |

***DAT = days after treatment

The impact of imazamox in a tank mixture with prohexadione-Ca when compared to a single application of either component against *orobanche* sp. (ORASS; application at BBCH 16-18) is demonstrated in table VII. The impact on infestation of the host plant (imizamox tolerant sunflower) was measured 21 days after treatment as a value between 1 and 10 where 1 is equal to no infestation and 10 is equal to high negative impact of the *Orobanche* on the host plant that eventually leads to the host plant to die off.

TABLE VII

| Product | | a.i. rate | a.i. unit | impact of host infestation with ORASS |
|---|---|---|---|---|
| Imazamox* | solo treatment | 15 | g/ha | 4 |
| Prohexadione-Ca** | solo treatment | 75 | g/ha | 6 |
| Imazamox* | tank mixture | 15 | g/ha | 2 |
| Prohexadione-Ca** | | 75 | g/ha | |

The invention claimed is:

1. A mixture comprising components:
    A) imazamox, an agriculturally acceptable salt, amide, ester, or thioester thereof; and
    B) one or two plant growth regulator(s) (PGR) selected from the group consisting of prohexadione, prohexadione-calcium, their agriculturally acceptable salts, and their derivatives; and
    wherein the weight ratio of A) to B) is from 1:100 to 100:1.

2. The mixture of claim 1, wherein component A) is imazamox.

3. The mixture of claim 1, wherein component B) is prohexadione.

4. The mixture of claim 1, wherein component B) is prohexadione-calcium.

5. The mixture of claim 1, which comprises as additional compound C) pyraclostrobin.

6. A composition comprising the mixture of claim 1, at least one inert liquid and/or solid carriers and, optionally, at least one surfactant.

7. A method for controlling parasitic weeds, comprising applying the mixture of claim 1 to the host plant, the weeds and/or their habitat.

8. The method of claim 7, wherein component A) is imazamox.

9. The method of claim 7, wherein component B) is prohexadione.

10. The method of claim 7, wherein component B) is prohexadione-calcium.

11. The method of claim 7, wherein the mixture of claim 1 further comprises as additional compound C) pyraclostrobin.

12. The method of claim 7, wherein the mixture further comprises at least one inert liquid and/or solid carriers and, optionally, at least one surfactant.

13. A method for controlling parasitic weeds comprising applying to a host plant, the weeds or their habitat
   A) imazamox, an agriculturally acceptable salt, amide, ester, or thioester thereof; and
   B) one or two plant growth regulator(s) (PGR) selected from the group consisting of prohexadione, prohexadione-calcium, their agriculturally acceptable salts, and their derivatives; and
wherein the weight ratio of A) to B) is from 1:100 to 100:1;
wherein said imazamox, agriculturally acceptable salt, amide, ester, or thioester thereof and said one or two plant growth regulator(s) (PGR) selected from the group consisting of prohexadione, prohexadione-calcium, their agriculturally acceptable salts, and their derivatives are applied simultaneously, or separately within one day.

* * * * *